(12) United States Patent
Sowinski et al.

(10) Patent No.: US 7,789,908 B2
(45) Date of Patent: Sep. 7, 2010

(54) ELASTOMERICALLY IMPREGNATED EPTFE TO ENHANCE STRETCH AND RECOVERY PROPERTIES FOR VASCULAR GRAFTS AND COVERINGS

(75) Inventors: Krzysztof Sowinski, Wallington, NJ (US); Ronald Rakos, Neshanic Station, NJ (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1319 days.

(21) Appl. No.: 10/179,484

(22) Filed: Jun. 25, 2002

(65) Prior Publication Data
US 2004/0024442 A1 Feb. 5, 2004

(51) Int. Cl.
*A61F 2/06* (2006.01)
(52) U.S. Cl. .................................. 623/1.45; 623/1.39
(58) Field of Classification Search .............. 623/1.1, 623/1.13, 1.25, 1.32, 1.39, 1.4, 1.46–1.48, 623/11.11, 12, 23.64–23.68, 23.7, 23.71, 623/1.45; 606/151, 191–200; 600/37; 427/2.24–2.26
See application file for complete search history.

(56) References Cited

U.S. PATENT DOCUMENTS

| | | | |
|---|---|---|---|
| 3,953,566 A | 4/1976 | Gore | |
| 3,962,153 A | 6/1976 | Gore | |
| 4,177,334 A | 12/1979 | Okita | |
| 4,187,390 A | 2/1980 | Gore | |
| 4,304,010 A | 12/1981 | Mano | |
| 4,321,711 A | 3/1982 | Mano | |
| 4,784,659 A * | 11/1988 | Fleckenstein et al. | 623/1.45 |
| 4,816,339 A | 3/1989 | Tu et al. | |
| 4,822,361 A * | 4/1989 | Okita et al. | 623/23.71 |
| 4,877,661 A | 10/1989 | House et al. | |
| 4,955,899 A | 9/1990 | Della Corna et al. | |
| 5,026,513 A | 6/1991 | House et al. | |
| 5,026,591 A | 6/1991 | Henn et al. | |
| 5,133,742 A | 7/1992 | Pinchuk | |
| 5,152,782 A | 10/1992 | Kowligi et al. | |
| 5,192,310 A | 3/1993 | Herweck et al. | |
| 5,308,664 A * | 5/1994 | House et al. | 428/34.9 |
| 5,397,628 A * | 3/1995 | Crawley et al. | 442/221 |
| 5,628,782 A | 5/1997 | Myers et al. | |

(Continued)

FOREIGN PATENT DOCUMENTS

EP 0 615 832 A1 9/1994

(Continued)

OTHER PUBLICATIONS

International Search Report issued in International Application No. PCT/US03/13747 filed May 1, 2003.

*Primary Examiner*—Corrine McDermott
*Assistant Examiner*—Cheryl Miller
(74) *Attorney, Agent, or Firm*—Vidas, Arrett & Steinkraus

(57) ABSTRACT

An elastomerically recoverable PTFE material is provided including a longitudinally compressed fibrils of ePTFE material penetrated by elastomeric material within the pores defining the elastomeric matrix. The elastomeric matrix and the compressed fibrils cooperatively expand and recover without plastic deformation of the ePTFE material. The material may be used for various prosthesis, such as a vascular a prosthesis like a patch, a graft and an implantable tubular stent. Further, a method of producing the elastomerically recoverable PTFE material is provided herein.

10 Claims, 3 Drawing Sheets

U.S. PATENT DOCUMENTS

| | | |
|---|---|---|
| 5,653,747 A | 8/1997 | Dereume |
| 5,665,114 A | 9/1997 | Weadock et al. |
| 5,716,660 A | 2/1998 | Weadock et al. |
| 5,904,967 A | 5/1999 | Ezaki et al. |
| 6,099,557 A | 8/2000 | Schmitt |
| 6,156,064 A | 12/2000 | Chouinard |
| 6,447,542 B1* | 9/2002 | Weadock ............. 623/11.11 |
| 6,673,455 B2* | 1/2004 | Zumbrum et al. ......... 428/421 |
| 6,743,253 B2* | 6/2004 | Phaneuf et al. .......... 623/1.46 |
| 6,929,768 B2* | 8/2005 | Sridharan et al. .......... 264/400 |
| 6,946,173 B2* | 9/2005 | Lim et al. ................ 428/35.2 |
| 6,976,952 B1* | 12/2005 | Maini et al. ................ 600/36 |
| 7,244,271 B2* | 7/2007 | Lentz et al. ............. 623/1.44 |
| 2002/0151009 A1* | 10/2002 | Ni et al. .................... 435/183 |
| 2003/0017775 A1* | 1/2003 | Sowinski et al. ........... 442/315 |
| 2003/0139806 A1* | 7/2003 | Haverkost et al. .......... 623/1.33 |
| 2003/0211264 A1* | 11/2003 | Farnsworth et al. ........ 428/36.9 |
| 2004/0167606 A1* | 8/2004 | Chouinard ................ 623/1.13 |
| 2006/0264138 A1* | 11/2006 | Sowinski et al. ........... 442/315 |

FOREIGN PATENT DOCUMENTS

| | | |
|---|---|---|
| JP | 5-509236 | 12/1993 |
| WO | WO 9501190 * | 1/1995 |
| WO | WO 9703812 A1 * | 2/1997 |
| WO | 00/09041 | 2/2000 |

* cited by examiner

DIRECTION OF EXPANSION

DIRECTION OF EXPANSION
DIRECTION OF COMPRESSION

DIRECTION OF COMPRESSION

DIRECTION OF COMPRESSION

ELASTOMERICALLY IMPREGNATED EPTFE TO ENHANCE STRETCH AND RECOVERY PROPERTIES FOR VASCULAR GRAFTS AND COVERINGS

FIELD OF THE INVENTION

The present invention relates generally to an elastomerically recoverable PTFE which is made from expanded, porous polytetrafluoroethylene (ePTFE) and impregnated with elastomer to be longitudinally compliant for allowing at least a portion of the ePTFE structure to stretch and recover along the longitudinal axis thereof.

BACKGROUND OF RELATED TECHNOLOGY

It is well known in the art that polymers, such as polytetrafluoroethylene (PTFE), are used to form a prosthesis. A tubular graft may be formed by stretching and expanding PTFE into a structure referred to as expanded polytetrafluoroethylene (ePTFE). Tubes formed of ePTFE exhibit certain beneficial properties as compared with textile prostheses. The expanded PTFE tube has a unique structure defined by nodes interconnected by fibrils. The node and fibril structure defines pores that facilitate a desired degree of tissue ingrowth while remaining substantially fluid-tight. Tubes of ePTFE may be formed to be exceptionally thin and yet exhibit the requisite strength necessary to serve in the repair or replacement of a body lumen. The thinness of the ePTFE tube facilitates ease of implantation and deployment with minimal adverse impact on the body.

While exhibiting certain superior attributes, ePTFE material is not without certain disadvantages. One disadvantage is the porosity of the ePTFE structure which permits cellular ingrowth. The ingrowth is undesirable if one uses the ePTFE material as a temporary graft to bridge vessels and it is desired to have clear access to the ePTFE graft for replacement or removal.

U.S. Pat. No. 5,665,114 to Weadock et al. discloses an implantable prosthesis made of ePTFE wherein the pores are filled with an in situ cross-linkable biocompatible and biodegradable material. The bio-material may be applied to the ePTFE using force to fill the pores with a dispersion or solution of the biomaterial, which is subsequently insolubilized therein.

U.S. Pat. No. 5,152,782 to Kowligi et al. discloses a non-porous elastomeric coating on a PTFE graft. The elastomeric coating is made of polyurethanes or silicone rubber elastomers. The elastomeric coating is applied to the graft by radially expanding the PTFE graft, and dipping or spraying the graft with the elastomeric coating. The radial expansion is controlled to ensure that the polymer coating penetration is restricted to the outer layers of the PTFE tube.

Another disadvantage is the ePTFE material has a tendency to leak blood at suture holes and often propagate a tear line at the point of entry of the suture. The suture holes in ePTFE do not self-seal due to the inelasticity of ePTFE material. As a result, numerous methods of orienting the node and fibril structure have been developed to prevent tear propagation. These processes are often complicated and require special machinery and/or materials to achieve this end. Prior art suggests encapsilling the ePTFE material with a liquid elastomer layer, the elastomer fills in and seals that suture hole.

U.S. Pat. No. 5,192,310 to Herweck et al. discloses a self-sealing PTFE or ePTFE vascular graft having a primary and secondary lumen. The primary lumen is to accommodate blood flow. The secondary lumen shares the outer wall as a common wall with the primary lumen. The secondary lumen is filled with a non-biodegradable elastomer material, such as silicone rubber, polyurethane, polyethers or fluoropolymers.

U.S. Pat. No. 5,904,967 to Ezaki et al. discloses a puncture resistant bio-compatible medical material for use on as grafts or artificial blood vessels. The puncture resistant material is sandwiched between two porous layers of the graft. The porous layers may be made of polyester resin or polyethylene terephthalate/polybuthylene terephthalate. The puncture resistant layer may be a styrene and/or olefin elastomer or isoprene derivatives. The layers are bonded by an adhesive or by fusion with heat.

Another problem is that ePTFE material exhibits a relatively low degree of longitudinal compliance. Expanded PTFE is generally regarded as an inelastic material. It has little memory and stretching results in deformation. In those instances when a surgeon will misjudge the length of the graft that is required to reach between the selected artery and vein, the surgeon may find that the graft is too short to reach the targeted site once the graft has been tunneled under the skin. Expanded PTFE vascular grafts typically exhibit minimal longitudinal compliance, and hence the graft does not stretch significantly along its longitudinal axis. Accordingly, in such cases, the surgeon must then remove the tunneled graft from below the skin and repeat the tunneling procedure with a longer graft.

Elasticity of an ePTFE vascular graft is important when used for bypass implants such as an axillofemoral bypass graft, wherein the vascular graft extends between the femoral artery in the upper leg to the axillary artery in the shoulder, as well as a femoropopliteal bypass graft extending below the knee. Such bypass grafts often place restrictions upon the freedom of movement of the patient in order to avoid pulling the graft loose from its anchor points. For example, in the case of the axillofemoral bypass graft, sudden or extreme movements of the arm or shoulder must be entirely avoided. Similarly, in the case of the femoropopliteal bypass graft, bending the knee can place dangerous stress upon the graft. The above-described restricted movement is due largely to the inability of the ePTFE vascular graft to stretch along its longitudinal axis when its associated anchor points are pulled apart from one another. Such restrictive movement is especially important during the early period of healing following implantation when there is still little tissue incorporation into the graft and it can move within the subcutaneous tunnel.

It is desirable to incorporate elastomeric properties into the PTFE. This incorporation is difficult because PTFE is a hydrophobic material making it difficult to wet with the hydro-based elastomers, and the elastomers are hydrophilic making them naturally attracted to other elastomeric molecules. When elastomeric material is applied to PTFE the two materials repel each other and the elastomer flow away from the nodes to a less hydrophobic area, the pores. The pores between the fibrils, are too small for the elastomeric material to penetrate. Thus, the elastomer remains on the surface of the fibrils and coat the exterior of PTFE.

Prior art suggests surface coating the ePTFE material with elastomer by dipping, spraying, or adhesive bonding. One disadvantage is that the coating may flake or separate from the ePTFE material, as well as add to the thickness of the ePTFE material.

U.S. Pat. No. 4,304,010 to Mano discloses a tubular prosthesis which is made of PTFE with a porous elastomeric coating on the outer surface. The elastomeric coating, which may be cross-linked, is described as being fluorine rubber, silicone rubber, urethane rubber, acrylic rubber or natural rubber, and may be applied to the PTFE prosthesis by wrapping, dipping, spraying or use of negative pressure.

U.S. Pat. No. 5,026,591 to Henn et al. discloses a coating product which contains a substrate and scaffolding, such as PTFE or ePTFE, where the pores are filled with a thermoplastic or thermosetting resin. The substrate may be of a diverse selection; i.e., woven, non-woven, fabric, paper, or porous polymer. Application of the resin to the PTFE substrate uses rollers to provide a controlled even coating.

U.S. Pat. No. 5,653,747 to Dereume discloses a stent to which a graft is attached. The graft component is produced by extruding polymer in solution into fibers from a spinnerette onto a rotating mandrel. A stent may be placed over the fibers while on the mandrel and then an additional layer of fibers spun onto the stent. The layer of layers of fibers may be bonded to the stent and/or one another by heat or by adhesives. The porous coating may be made from a polyurethane or polycarbonate urethane which may be bonded by heat or by adhesion to the support.

U.S. Pat. No. 4,321,711 to Mano discloses a vascular prosthesis of PTFE with an anti-coagulant coating and bonded to its outer surface a porous elastomer coating containing a coagulant. The elastomer is used in its crosslinked state and is made of fluorine rubber, silicone rubber, urethane rubber, acrylic rubber or natural rubber. The elastomeric coating is bonded to the PTFE by dipping, spraying and/or applying negative pressure to inside wall PTFE to pass elastomer through the wall.

U.S. Pat. No. 4,955,899 to Della Conna et al. discloses a longitudinally compliant PTFE graft. The PTFE tube is longitudinally compressed and the outer wall of the PTFE is coated with a biocompatible material, such as polyurethanes or silicone rubber elastomers. The coating is applied by compressing the PTFE tube on a mandrel, and dipping or spraying the PTFE with the elastomer. The elastomer coating is restricted to the outer layers of the PTFE tube. The elastomer coated PTFE is dried while in the compressed state.

Other prior art suggests bonding a separate layer of elastomer to the ePTFE material to enhance the elasticity. One disadvantage is the added thickness of the PTFE. Another disadvantage, as stated above with the elastomer coatings, is the layers will separate over time and can flake off the PTFE. Examples of bonding layers of elastomer to PTFE is discussed below.

U.S. Pat. No. 4,816,339 to Tu et al. discloses a bio-compatible material made from layers of PTFE and hydrophobic PTFE fibers coated with an elastomer mixture. The bio-compatible material disclosed is a PTFE layer, elastomer/PTFE mixed layer, elastomer layer and hydrophilic monomer fibrous elastomer matrix layer. The elastomer layer is made from polyurethane. The elastomer is applied to the combined PTFE layer by heating and radially expanding the combined PTFE layers and dipping or spraying the combined PTFE layers with elastomer.

U.S. Pat. No. 5,628,782 to Myers et al. discloses a biocompatible base material such as PTFE or ePTFE with an outer deflectably secured outer covering. The preferably outer covering is non-elastic porous film or fibers, preferable PTFE. The outer covering is secured to the base by use of an adhesive.

U.S. Pat. No. 6,156,064 to Choumard discloses a braided self-expandable stent-graft-membrane. This three layer invention has an interior graft layer which is braided PET, PCV or PU fibers; a middle layer which is the stent; and an exterior membrane layer which is a silicone or polycarbonate methane. The membrane layer is applied to the exterior of the stent layer by dipping, by braiding, by spraying or by fusing; which includes use of adhesive, solvent bonding or thermal and/or pressure bonding.

It is desirable to provide an ePTFE material that achieves many of the above-stated benefits without the resultant disadvantages associated therewith and disadvantages of similar conventional products. It is also desirable to make this elastomerically recoverable PTFE material available to be manufactured in a variety of used such as an implantable prosthesis, patch material, graft, or stent.

SUMMARY OF THE INVENTION

The present invention provides an elastomerically recoverable PTFE material that was made of ePTFE material, defined by nodes and fibrils, and an elastomeric matrix. The fibrils were longitudinally compressed, defining a pore size that is a sufficient size to permit penetration of an elastomeric material. The elastomeric material penetrated the pores, which defined the elastomeric matrix within the pores. The compressed fibrils and elastomeric matrix cooperatively permitted longitudinal expansion and elastomeric recovery without plastic deformation of the ePTFE material.

The elastomerically recoverable PTFE material is used for a variety of applications, such as implantable prosthesis. This includes vascular prosthesis such as patches, grafts or implantable tubular stent graft with a longitudinally expandable stent.

Another aspect of this invention was to provide a method of producing an elastomerically recoverable PTFE material. The steps to produce this material are discussed below.

First step was to provide the ePTFE material defined by the nodes, fibrils and pores with the required dimensions and specifications to produce the desired end product. The ePTFE material varied in their dimensions and specifications such as an ePTFE tube defined by an internal diameter and an external diameter.

Next, the fibrils were compressed longitudinally, the pore size was sufficiently large enough to permit the elastomeric material to penetrate the pores. The compression step was performed by a variety of techniques. For example, the ePTFE tube was pulled over a mandrel with an outer diameter approximately the same size as the internal diameter of the ePTFE tube. The entire ePTFE tube or at least a portion of the ePTFE tube was compressed along the longitudinal axis of the tube while the tube was supported by the mandrel. The ePTFE tube was compressed uniformly along the entire length or any portion thereof of the ePTFE material.

Then the elastomeric material was applied within the pores to provide a structurally integral elastomerically recoverable PTFE material. Elastomer was applied by a variety of techniques, such as dipping, spraying or brushing techniques. The elastomeric material was applied over the entire longitudinally compressed ePTFE material or to any portion thereof.

One advantage of this method was that the compression step and the application steps were interchangeable to produce an elastomerically recoverable PTFE material with various properties, such as different expansion ratios. The various properties of the final product were produced by performing the compression step prior to, between, and/or after the application of the elastomeric material.

Finally, the elastomeric material was dried within the pores while the fibrils were still longitudinally compressed which defined the elastomeric matrix. An advantage of this method was that the drying step was performed between applications of the elastomeric material or after completion of all the elastomeric material application depending on the desired end product use.

DETAILED DESCRIPTION OF THE PREFERRED EMBODIMENT

The invention described herein provides an elastomerically recoverable PTFE material which has a combination of high stretch and elastomeric compression, high flexibility, and high strength without deformation of the material. In this regard it not only exceeds previously available PTFE products, but is unique among elastomer coated plastic materials.

Expanded PTFE

Figure 1:
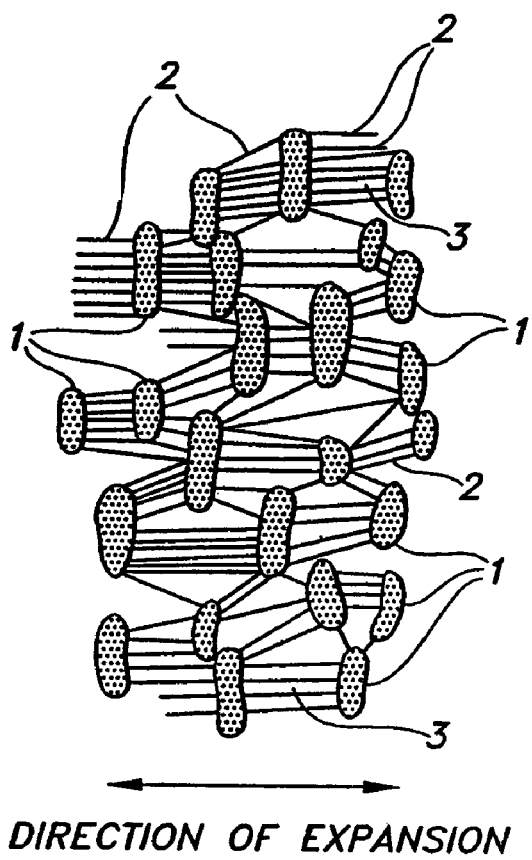
FIG. 1 is a schematic representation of the microstructure of ePTFE material defined by nodes 1, fibrils 2 and pores 3.

The precursor for this invention is porous ePTFE which is well known in the art and is described in detail, for example, in U.S. Pat. Nos. 3,953,566 and 3,962,153, which is incorporated herein by reference as shown in FIG. 1. Generally, paste-forming techniques are used to convert the polymer in paste form to a shaped article which is then expanded, after removing the lubricant, by stretching it in one or more directions; and while it is held in its stretched condition it is heated to at least 348° C. after which it is cooled. The porosity that is produced by the expansion is retained for there is little or no coalescence or shrinking upon releasing the cooled, final article.

Paste-forming of dispersion polymerized poly(tetrafluoroethylene) is well known commercially. Extrusions of various cross-sectional shapes such as tubes, rods and tapes are commonly obtained from a variety of tetrafluoroethylene resins, and other paste-forming operations such as calendering and molding are practiced commercially. The steps in paste-forming processes include mixing the resin with a lubricant such as odorless mineral spirits and carrying out forming steps in which the resin is subjected to shear, thus making the shaped articles cohesive. The lubricant is removed from the extruded shape usually by drying.

The paste-formed, dried, unsintered shapes are expanded by stretching them in one or more directions under certain conditions so that they become substantially much more porous and stronger. Expansion increases the strength of PTFE resin within preferred ranges of rate of stretching and preferred ranges of temperature. It has been found that techniques for increasing the crystallinity, such as annealing at high temperatures just below the melt point, improve the performance of the resin in the expansion process.

The porous microstructure of the ePTFE material is affected by the temperature and the rate at which it is expanded. The structure consists of nodes 1 interconnected by very small fibrils 2. In the case of uniaxial expansion the nodes 1 are elongated, the longer axis of a mode being oriented perpendicular to the direction of expansion. The fibrils 2 which interconnected the nodes 1 are oriented parallel to the direction of expansion. These fibrils 2 appear to be characteristically wide and thin in cross-section, the maximum width being equal to about 0.1 micron (1000 angstroms) which is the diameter of the crystalline particles. The minimum width may be one or two molecular diameters or in the range of 5 or 10 angstroms. The nodes 1 may vary in size from about 400 microns to less than a micron, depending on the conditions used in the expansion. Products which have expanded at high temperatures and high rates have a more homogeneous structure, i.e., they have smaller, more closely spaced nodes 1 and these nodes 1 are interconnected with a greater number of fibrils 2.

When the ePTFE material is heated to above the lowest crystalline melting point of the poly(tetrafluoroethylene), disorder begins to occur in the geometric order of the crystallites and the crystallinity decreases, with concomitant increase in the amorphous content of the polymer, typically to 10% or more. These amorphous regions within the crystalline structure appear to greatly inhibit slippage along the crystalline axis of the crystallite and appear to lock fibrils and crystallites so that they resist slippage under stress. Therefore, the heat treatment may be considered an amorphous locking process. The important aspect of amorphous locking is that there be an increase in amorphous content, regardless of the crystallinity of the starting resins. Whatever the explanation, the heat treatment above 348° C. causes a surprising increase in strength, often doubling that of the unheated-treated material.

The preferred thickness of ePTFE material ranges from 0.025 millimeter to 2.0 millimeters; the preferred internodal distance within such ePTFE material ranges from 20 micrometers to 200 micrometers. The longitudinal tensile strength of such ePTFE material is preferably equal to or greater than 1,500 psi, and the radial tensile strength of such ePTFE material is preferably equal to or greater than 400 psi.

Elastometric Material

The elastomeric material of this invention was biocompatible elastomer such as polyurethanes, adhesive solutions and elastomeric adhesive solutions. Suitable candidates for use as an elastomer typically have a Shore hardness rating between 70A and 75D. Most of the above-mentioned elastomers can be chemically or biologically modified to improve biocompatability; such modified compounds are also candidates for use in forming elastomeric material impregnation.

Apart from biocompatability, other requirements of an elastomer to be a suitable candidate for use as elastomeric material impregnation are that the elastomer be sufficiently elastic to maintain compressed portions of ePTFE material in the compressed condition when it is not being stretched. The elastomer should also be sufficiently elastic to effect closure of suture holes formed by a suture needle. The amount of elastomeric material needed is the amount to impregnate the ePTFE and provide the desired elasticity for the end product use, without supersaturating the ePTFE and creating an exterior outer coatings of elastomer on the ePTFE. Yet another requirement of such elastomers is that they be easily dissolvable in low boiling point organic solvents such as tetrahydrofuran, methylene chloride, trichloromethane, dioxane, dimethylformamide, and dimethylacetamide (DMAc) by way of example. Finally, suitable elastomeric materials should lend themselves to application by either the dip, brush or spray coating methods described below.

The term elastomeric as used herein refers to a substance having the characteristic that it tends to resume an original shape after any deformation thereto, such as stretching, expanding or compression. It also refers to a substance which has a non-rigid structure, or flexible characteristics in that it is not brittle, but rather has compliant characteristics contributing to its non-rigid nature.

The polycarbonate urethane polymers particularly useful in the present invention are more fully described in U.S. Pat. Nos. 5,133,742 and 5,229,431 which are incorporated in their entirety herein by reference. These polymers are particularly resistant to degradation in the body over time and exhibit exceptional resistance to cracking in vivo. These polymers are segmented polyurethanes which employ a combination of hard and soft segments to achieve their durability, biostability, flexibility and elastomeric properties.

The polycarbonate urethanes useful in the present invention are prepared from the reaction of an aliphatic or aromatic polycarbonate macroglycol and a diisocyanate n the presence of a chain extender. Aliphatic polycarbonate macroglycols such as polyhexane carbonate macroglycols and aromatic diisocyanates such as methylene diisocyanate are most desired due to the increased biostability, higher intramolecular bond strength, better heat stability and flex fatigue life, as compared to other materials.

The polycarbonate urethanes particularly useful in the present invention are the reaction products of a macroglycol, a diisocyanate and a chain extender.

A polycarbonate component is characterized by repeating

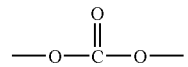

units, and a general formula for a polycarbonate macroglycol is as follows:

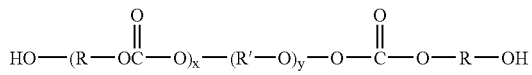

wherein x is from 2 to 35, y is 0, 1 or 2, R either is cycloaliphatic, aromatic or aliphatic having from about 4 to about 40 carbon atoms or is alkoxy having from about 2 to about 20 carbon atoms, and wherein R' has from about 2 to about 4 linear carbon atoms with or without additional pendant carbon groups.

Examples of typical aromatic polycarbonate macroglycols include those derived from phosgene and bisphenol A or by ester exchange between bisphenol A and diphenyl carbonate such as (4,4'-dihydroxy-diphenyl-2,2'-propane) shown below, wherein n is between about 1 and about 12.

Typical aliphatic polycarbonates are formed by reacting cycloaliphatic or aliphatic diols with alkylene carbonates as shown by the general reaction below:

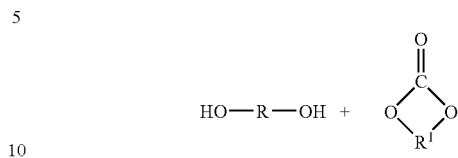

wherein R is cyclic or linear and has between about 1 and about 40 carbon atoms and wherein $R^1$ is linear and has between about 1 and about 4 carbon atoms.

Typical examples of aliphatic polycarbonate diols include the reaction products of 1,6-hexanediol with ethylene carbonate, 1,4-butanediol with propylene carbonate, 1,5-pentanediol with ethylene carbonate, cyclohexanedimethanol with ethylene carbonate and the like and mixtures of above such as diethyleneglycol and cyclohexanedimethanol with ethylene carbonate.

When desired, polycarbonates such as these can be copolymerized with components such as hindered polyesters, for example phthalic acid, in order to form carbonate/ester copolymer macroglycols. Copolymers formed in this manner can be entirely aliphatic, entirely aromatic, or mixed aliphatic and aromatic. The polycarbonate macroglycols typically have a molecular weight of between about 200 and about 4000 Daltons.

Diisocyanate reactants according to this invention have the general structure OCN—R'—NCO, wherein R' is a hydrocarbon that may include aromatic or nonaromatic structures, including aliphatic and cycloaliphatic structures. Exemplary isocyanates include the preferred methylene diisocyanate (MDI), or 4,4-methylene bisphenyl isocyanate, or 4,4'-diphenylmethane diisocyanate and hydrogenated methylene diisocyanate (HMDI). Other exemplary isocyanates include hexamethylene diisocyanate and other toluene diisocyanates such as 2,4-toluene diisocyanate and 2,6-toluene diisocyanate, 4,4' tolidine diisocyanate, m-phenylene diisocyanate, 4-chloro-1,3-phenylene diisocyanate, 4,4-tetramethylene diisocyanate, 1,6-hexamethylene diisocyanate, 1,10-decamethylene diisocyanate, 1,4-cyclohexylene diisocyanate, 4,4'-methylene bis (cyclohexylisocyanate), 1,4-isophorone diisocyanate, 3,3'-dimethyl-4,4'-diphenylmethane diisocyanate, 1,5-tetrahydronaphthalene diisocyanate, and mixtures of such diisocyanates. Also included among the isocyanates applicable to this invention are specialty isocyanates containing sulfonated groups for improved hemocompatibility and the like.

Suitable chain extenders included in this polymerization of the polycarbonate urethanes should have a functionality that is equal to or greater than two. A preferred and well-recognized chain extender is 1,4-butanediol. Generally speaking, most diols or diamines are suitable, including the ethylenediols, the propylenediols, ethylenediamine, 1,4-butanediamine methylene dianiline heteromolecules such as ethano-

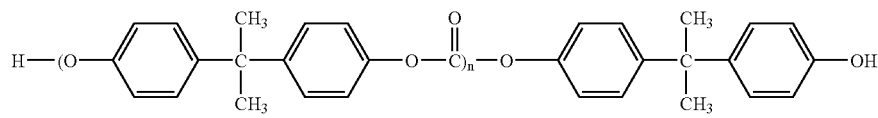

lamine, reaction products of said diisocyanates with water and combinations of the above.

The polycarbonate urethane polymers according to the present invention should be substantially devoid of any significant ether linkages (i.e., when y is 0, 1 or 2 as represented in the general formula hereinabove for a polycarbonate macroglycol), and it is believed that ether linkages should not be present at levels in excess of impurity or side reaction concentrations. While not wishing to be bound by any specific theory, it is presently believed that ether linkages account for much of the degradation that is experienced by polymers not in accordance with the present invention due to enzymes that are typically encountered in vivo, or otherwise, attack the ether linkage via oxidation. Live cells probably catalyze degradation of polymers containing linkages. The polycarbonate urethanes useful in the present invention avoid this problem.

Because minimal quantities of ether linkages are unavoidable in the polycarbonate producing reaction, and because these ether linkages are suspect in the biodegradation of polyurethanes, the quantity of macroglycol should be minimized to thereby reduce the number of ether linkages in the polycarbonate urethane. In order to maintain the total number of equivalents of hydroxyl terminal groups approximately equal to the total number of equivalents of isocyanate terminal groups, minimizing the polycarbonate soft segment necessitates proportionally increasing the chain extender hard segment in the three component polyurethane system. Therefore, the ratio of equivalents of chain extender to macroglycol should be as high as possible. A consequence of increasing this ratio (i.e., increasing the amount of chain extender with respect to macroglycol) is an increase in hardness of the polyurethane. Typically, polycarbonate urethanes of hardnesses, measured on the Shore scale, less than 70A show small amounts of biodegradation. Polycarbonate urethanes of Shore 75A and greater show virtually no biodegradation.

The ratio of equivalents of chain extender to polycarbonate and the resultant hardness is a complex function that includes the chemical nature of the components of the urethane system and their relative proportions. However, in general, the hardness is a function of the molecular weight of both chain extender segment and polycarbonate segment and the ratio of equivalents thereof. Typically, the 4,4'-methylene bisphenyl diisocyanate (MDI) based systems, a 1,4-butanediol chain extender of molecular weight 90 and a polycarbonate urethane of molecular weight of approximately 2000 will require a ratio of equivalents of at least about 1.5 to 1 and no greater than about 12 to 1 to provide non-biodegrading polymers. Preferably, the ratio should be at least about 2 to 1 and less than about 6 to 1. For a similar system using a polycarbonate glycol segment of molecular weight of about 1000, the preferred ration should be at least about 1 to 1 and no greater than about 3 to 1. A polycarbonate glycol having a molecular weight of about 500 would require a ratio in the range of about 1.2 to about 1.5:1.

The lower range of the preferred ratio of chain extender to macroglycol typically yields polyurethanes of Shore 80A hardness. The upper range of ratios typically yields polycarbonate urethanes on the order of Shore 75D. The preferred elastomeric and biostable polycarbonate urethanes for most medical devices would have a Shore hardness of approximately 85A.

Generally speaking, it is desirable to control somewhat the cross-linking that occurs during polymerization of the polycarbonate urethane polymer. A polymerized molecular weight of between about 80,000 and about 200,000 Daltons, for example on the order of about 120,000 Daltons (such molecular weights being determined by measurement according to the polystyrene standard), is desired so that the resultant polymer will have a viscosity at a solids content of 43% of between about 900,000 and about 1,800,000 centipoise, typically on the order of about 1,000,000 centipoise. Cross-linking can be controlled by avoiding an isocyanate-rich situation. Of course, the general relationship between the isocyanate groups and the total hydroxyl (and/or amine) groups of the reactants should be on the order of approximately 1 to 1. Cross-linking can be controlled by controlling the reaction temperatures and shading the molar ratios in a direction to be certain that the reactant charge is not isocyanate-rich; alternatively a termination reactant such as ethanol can be included in order to block excess isocyanate groups which could result in cross-linking which is greater than desired.

Concerning the preparation of the polycarbonate urethane polymers, they can be reacted in a single-stage reactant charge, or they can be reacted in multiple states, preferably in two stages, with or without a catalyst and heat. Other components such as antioxidants, extrusion agents and the like can be included, although typically there would be a tendency and preference to exclude such additional components when a medical-grade polymer is being prepared.

Additionally, the polycarbonate urethane polymers can be polymerized in suitable solvents, typically polar organic solvents in order to ensure a complete and homogeneous reaction. Solvents include dimethylacetamide, dimethylformamnide, dimethylsulfoxide toluene, xylene, m-pyrrol, tetrahydrofiaran, cyclohexanone, 2-pyrrolidone, and the like, or combinations thereof. These solvents can also be used to delivery the polymers to the ePTFE layer of the present invention.

A particularly desirable polycarbonate urethane is the reaction product of polyhexamethylenecarbonate diol, with methylene bisphenyl diisocyanate and the chain extender 1,4-butanediol.

The solvents used in the present invention must be capable of wetting the membrane surface and penetrating the pores. In the case of ePTFE membranes, wettability of the surface is difficult to accomplish due to the surface tension properties of the fluoropolymeric structure. Many solvents will not readily wet the surface of ePTFE sufficiently to penetrate the pores. Thus, the choice of elastomeric material and solvent must be made with these properties in mind. The elastomeric material must be sufficiently dissolvable or softened at the interface to flow and penetrate into the membrane pores.

Progressive wetting of the membrane permits the elastomer to enter the pores of the ePTFE material and thus contribute to achieving the advantages of enhanced stretch and recoverability of the present invention. Membranes formed of a hydrophobic material such as ePTFE are difficult to wet. The type of solvent employed must be both capable of dissolving the elastomeric material and of wetting the surface of the membrane. Suitable solvent materials, which have been found to be useful with polyurethane elastomeric materials and ePTFE membranes include, without limitation, dimethylacetamide, tetrahydrofuran, ethers, methylene chloride, chloroform, toluene and mixtures thereof. The mixture of solvent and elastomeric material provides a balance of wetting and solvent properties which are particularly effective at causing penetration and entrapment of the elastomeric material within the pores of the ePTFE.

Other solvents may be employed provided they are capable of wetting the membrane, i.e., ePTFE surface, i.e., reducing surface tension such that the elastomeric material will flow into the porous microstructure, and are capable of sufficiently dissolving the elastomeric material to cause flow and penetration into the membrane. The solvents chosen should have little or no effect on the membrane and serve only as a means to infiltrate the microstructure and carry the elastomeric material therewith. The solvents are then removed by evaporation and the elastomeric material is permitted to dry and resolidify within the porous structure.

Examples of a suitable elastomeric material were sold under the trademark name "BIONATE" by Polymer Technology Group of Berkley, Calif. and "CORETHANE" by Corvita Corporation of Miami, Fla. Such elastomeric materials were designed to be dissolved in various solvents for use in solution casting, extruding or for coating of medical products. The polycarbonate urethane was dissolved in the solvent known as DMAc.

The method of formulating the liquefied elastomeric material was the same, as known in the art. This solution was prepared by dissolving polyurethane pellets in the above-described DMAc solvent in a heated glass reactor equipped with a cold water condenser held at 60 C. Such polyurethane pellets may also be dissolved in the solvent at room temperature through continuous stirring. The use of the heated reactor was preferred, as it dissolved the polyurethane pellets in a few hours, whereas the method of stirring the solution at room temperature took approximately two days.

The preferred solids content for "Corethane 2.5W30" was 7.5% by weight; however, the solids content have ranged up to 15% by weight, depending upon the specific polymer composition, the dip, brush, spray technique parameters, and the intended end uses. Various grades of Corethane solution are useful depending on the intended end use. Where multiple applications were employed, the composition of the elastomeric material were varied between the applied layers.

METHOD OF PRODUCING ELASTOMERICALLY EXPANDABLE EPTFE MATERIAL

In practicing the preferred method, the ePTFE starting material is initially in the form of a cylindrical tube having an inside diameter up to 50 millimeters. The length may vary depending on the intended end use.

(i) Longitudinal Compression Process

The compression process of the ePTFE took place either prior to, during or after the applications of the elastomeric material. The porous wall structure of the ePTFE easily allowed compression back to the starting length of the unexpanded PTFE tube structure before it was expanded during the manufacturing process. The fibrils 2 of the uncompressed ePTFE were longitudinally compressed which change the shape of the pore 3, and elastomer is permitted to penetrate into the polymeric matrix of the ePTFE. Nodes 1 that are forced closer together to allow the fibrils 2 to bow out or wrinkle, which may increase the distance between the fibrils 2, and change the pore 3 shape. The pore 3 which permit the elastomer to enter into this space defines the sufficient size of the pore. This sufficient size of the pore 3 is the range between the starting state and the overly compressed state. The starting state is where the node 1 is farthest apart from the opposite node 1 and the connecting fibrils 2 are taut between the two nodes 1. The overly compressed state is where the opposite nodes 1 are pushed together, creating two smaller pores 3, and the fibrils 2 are crushed as well. In this case the pore 3 space is too small to permit the elastomer to enter within this space. One way to compress the ePTFE was to pull the ePTFE tube over a cylindrical supporting mandrel with an outer diameter that about equal to the internal diameter of the ePTFE tube.

Figure 2:
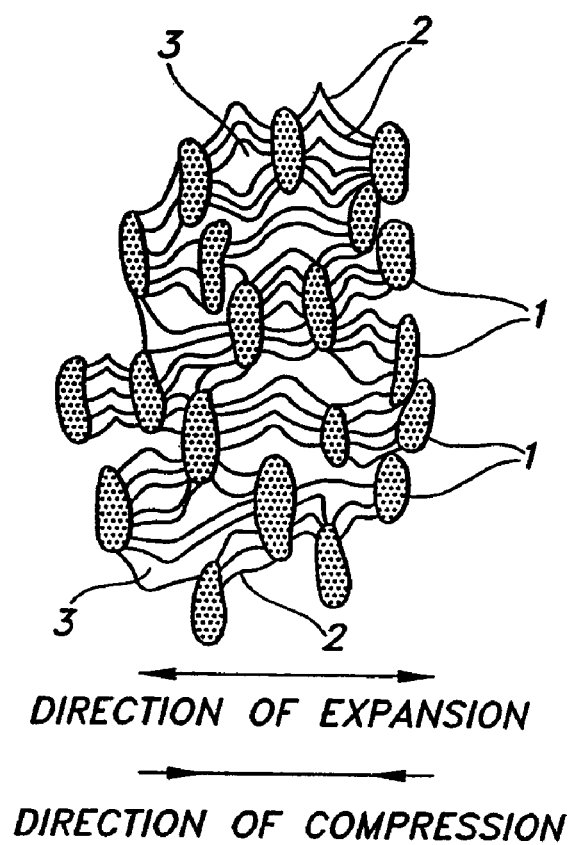
FIG. 2 and FIG. 3 are schematic representations of the microstructure of longitudinally compressed ePTFE material defined by nodes 1, longitudinally compressed fibrils 2 and pores 3.
Figure 3:
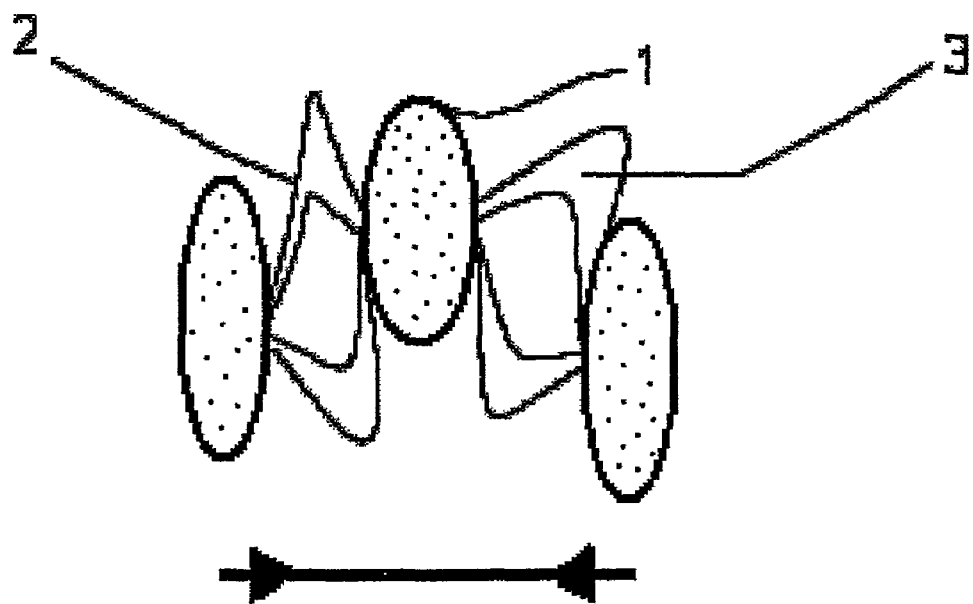

The ePTFE was compressed along the longitudinal axis of the ePTFE. The compression procedure was accomplished by mechanical or thermal procedures. The mechanical procedure included manually squeezing the ePTFE from both of its ends until a predetermined final compressed length is reached. The thermal procedure included evenly heating the portion of the ePTFE that is desired to be compressed. The compression step included uniformly compressing the PTFE tube along its entire length to produce a tube that stretched along its entire length up to 90% compression, or localized compression to satisfy the intended end use. The percent compression is defined as the ratio of the final compressed length to the initial uncompressed length. The desired percent compression depends upon the ePTFE manufactured expansion ratios, and depending upon the intended use of the final product. Visually the compressed ePTFE material appears to be denser because the internodal distance has been decreased, as a result of the nodes 1 being forced closer together. FIGS. 2 and 3 show the decreased distance between the nodes 1 limits the space available for the fibrils 2, resulting in the fibrils 2 crinkling, wrinkling or possibly folding. Visually the compressed ePTFE material appears to be wrinkled, crinkled or folded, the larger the compression ratio the more wrinkling was seen.

Once the whole or any section of the ePTFE material has been uniformly compressed along its length, as shown in FIGS. 2 and 3, it is secured on the mandrel by mechanical means such as Teflon tape or clamps about the ends of the compressed ePTFE tube.

(ii) Application of Elastomeric Material Process

Once the pore 3 is a sufficient size to permit penetration of the elastomeric material, the elastomer may be applied. The elastomeric material flowed into the pores 3 between the fibrils 2, the point of least repelling force, to escape the hydrophobic forces from the ePTFE material, nodes 1 and fibrils 2. The elastomeric material became entrapped between the pores 3 and embedded the internal fibrils 2 and nodes 1. The embedded fibrils 2 and nodes 1 acted as an internal structural support for the elastomeric webbing or matrix 4. As mentioned above, the longitudinal compression process was performed before, during or after the applications of the elastomeric material depending on the desired properties for the end-use product. The application process entailed initially dissolving the elastomer in a suitable solution as discussed above, defining the elastomeric material. The elastomeric material was then applied to the compressed and uncompressed ePTFE by various techniques including dip coating, brushing, spraying and the like For example, the elastomeric material was applied to the ePTFE by the method of dip coating which is known in the art by use of a dip coating machine. Attention must be placed on the parameters of the machine and length of the ePTFE to prevent an uneven application. The dip coating machine method of application consisted of the mandrel extended vertically downward from a motor which continuously rotated the mandrel and ePTFE material secured thereto (compressed or uncompressed ePTFE). Motor is, in turn, supported by a bracket adapted to travel vertically upward and downward. Bracket included a smooth bushing through which a smooth vertical support rod passes. Bushing was adapted to slide upwardly and downwardly along support rod. Bracket further included a threaded collar through which a threaded rotatable drive rod passes. The lowermost end of drive rod is secured to the drive shaft of a second motor which rotated in a first rotational direction to raise mandrel and which rotated in an opposing rotational direction to lower mandrel. Both motor and support rod were supported at their lower ends by a base. The upper end of support rod was fixedly secured to bracket which rotatably supported the upper end of drive rod. Motor of dip coating machine was initially operated to raise mandrel to its uppermost position. A tall, slender container containing the above-described solution was placed upon base immediately below mandrel. Motor was then operated in the reverse rotational direction to lower mandrel, and ePTFE material section secured thereto, into the solution. The variables controlled by dip coating machine include the speed at which mandrel was immersed and withdrawn and the rotational speed of mandrel. These parameters were controlled to ensure that the solution penetrates the ePTFE to allow for the impregnation of the elastomeric material.

Another example of applying the elastomeric material to the ePTFE material involved the use of spraying which was preformed by a spray coating machine. The elastomeric material to be sprayed is first prepared in the same manner as described above for the dip coating process. The elastomeric material was inserted within cylinder of a pump for delivery through a plastic tube to a spray nozzle. An inert gas, such as nitrogen, was also supplied to spray nozzle through connecting tube from supply tank. An inert gas was preferably used to minimize reactions which elastomeric material can undergo upon exposure to air and oxygen. The mandrel with the ePTFE was supported for rotation about a horizontal axis. One end of mandrel was coupled to the drive shaft of a first motor within motor housing, while the opposite end of mandrel was rotatably supported by bracket. Both motor housing and bracket were supported upon the base. The aforementioned first motor continuously rotated the mandrel at speeds of up to 500 rotations per minute. The spray nozzle was supported for reciprocal movement above and along mandrel. The spray nozzle was secured to support rod which included at its lowermost end a carriage. A threaded drive rod was coupled at a first end to the drive shaft of a second motor within motor housing for being rotated thereby. The opposite end of threaded drive rod was supported by and freely rotated within bracket. Threaded drive rod threadedly engaged a threaded collar within carriage. Accordingly, rotation of drive rod caused the carriage, and hence spray nozzle, to move in the directions designated by dual headed arrow, depending upon the direction of rotation of drive rod. A pair of micro switches which were periodically engaged by carriage and which, when actuated, reverse the direction of rotation of threaded drive rod in a manner which caused spray nozzle to reciprocate back and forth along mandrel. Spray nozzle made several passes along mandrel, repetitively spraying ePTFE material as it rotated. Spray nozzle was caused to travel at a linear speed of up to 50 centimeters per minute. The amount of elastomeric material resulted from this spraying process was determined by the speed of rotation of mandrel, the linear speed of spray nozzle, the concentration of the elastomeric material, as well as the rates of delivery of the elastomeric material. These rates of delivery ranged up to 5 milliliters per minute for the solution, and up to 5 liters per minute for the nitrogen gas. The spray application was repeated as needed to reach the desired properties and amount of elasticity for the end product use.

A final example of applying the elastomeric material to the ePTFE material involved the use of a brushing technique which was preformed by the same manner as the spraying machine by securing the mandrel and providing a means of rotation for even application. But instead of spraying the elastomeric material, it was evenly brushed onto the compressed or uncompressed ePTFE.

The number of elastomeric material applications ranged between 1 and 100 times, depending upon the concentration of the elastomeric material used in the application process, depending upon the application technique chosen and parameters of that technique, and depending upon the intended use of the end product.

While the application of elastomeric material by dipping, brushing and spraying methods described above were directed to the application of entire ePTFE material, those skilled in the art will appreciate that such application may be used on only portions of the compressed or uncompressed ePTFE material as well.

(iii) Drying Process

Figure 4:
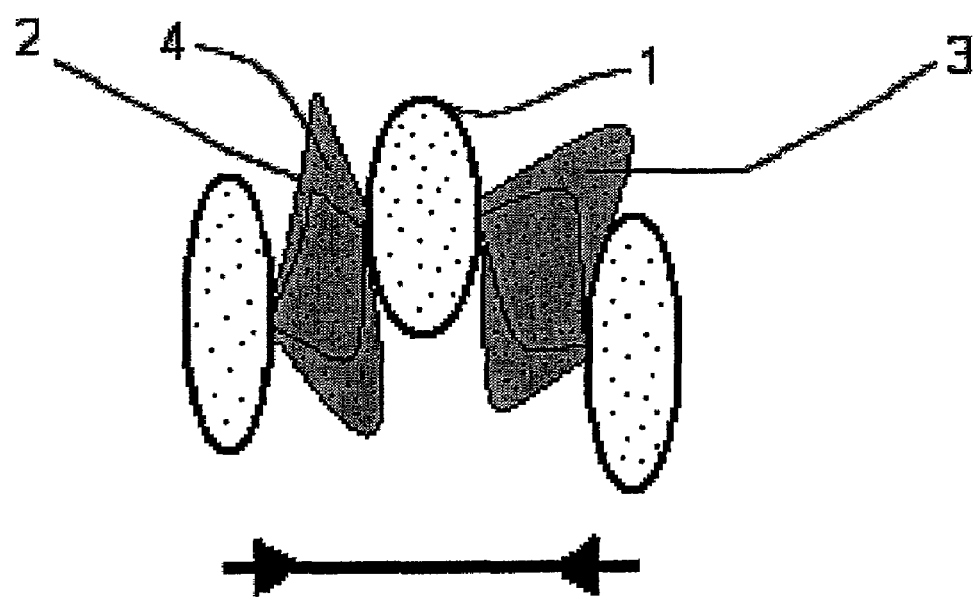
FIG. 4 is a schematic representation of the microstructure of the ePTFE material of the present invention, defined by nodes 1, longitudinally compressed fibrils 2 and elastomeric matrix 4 within the pores 3.

The drying process was performed upon the completion of the application of the elastomeric material, or between applications of the elastomeric material. The drying process solidified the elastomeric material within the pores 3, defining, the elastomeric matrix 4, by evaporating the solvent and completing the impregnation of the elastomeric material within the pores 3 of the ePTFE as shown in FIG. 4. The drying process depended on the solvent used, which can include placing the mandrel with the ePTFE into the oven or allowing the ePTFE to dry at ambient conditions over an extended period of time. The drying process evaporated some of the solvent if used between elastomer applications, or evaporated all of the solvent at the completion of the final product. Once the drying process was complete, the elastomerically recoverable ePTFE was removed from the mandrel. While the above describes the drying process and elastomeric application as separate steps, one can appreciate that the steps may be simultaneously occurring. For example, certain solvent concentrations used with the spray technique can evaporate at ambient temperatures upon application of the elastomer.

The elastomer matrix 4 serves two vital purposes; as a bonding agent basically holding the ePTFE in the compressed state, and as a recovery agent where after the material is longitudinally stretched the elastomer matrix recovers the material back to the compressed state without deformation.

The use of an elastomerically recoverable ePTFE tube as a vascular graft 5 implanted within a patient provided an axillofemoral bypass graft. The lower end of vascular graft was anchored to femoral artery, while the upper end of vascular graft was anchored to axillary artery. When conventional PTFE grafts were used to perform such a bypass, raising of the arm placed tension on graft, and placed stress upon the sutured ends of graft, sometimes caused such ends to pull loose from the points at which they were anastomosed to the aforementioned arteries. In contrast, the use of elastomerically recoverable ePTFE vascular graft 5 in such applications permitted the graft to be stretched without imparting undue stress upon the anchored ends and the graft recovers to the original size, thereby permitting the patient greater freedom of movement, more comfort and no need to replace due to flaking or deformation.

Figure 5:
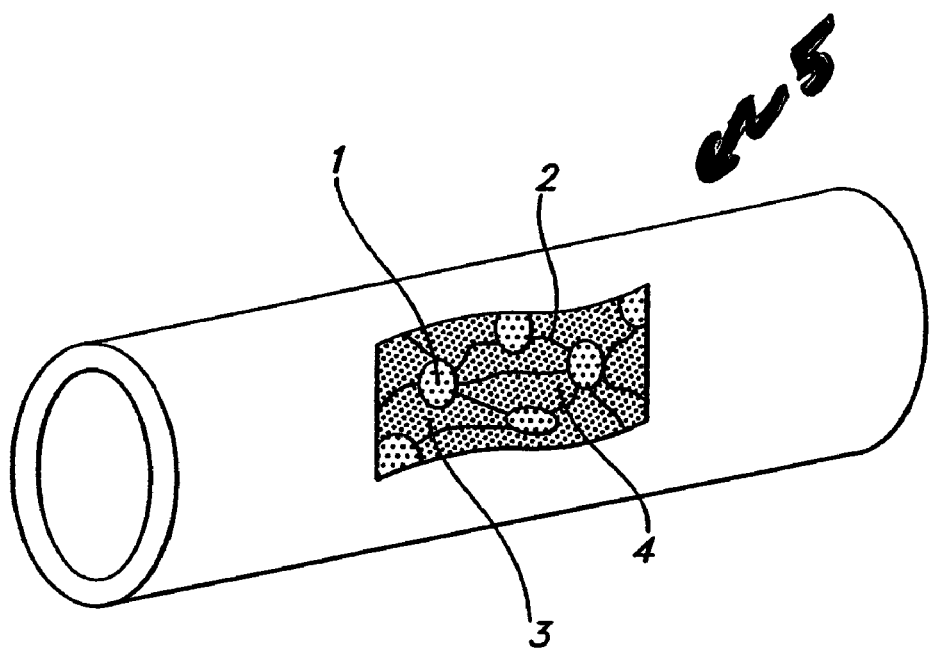
FIG. 5 is a schematic representation of the ePTFE materials of the present invention formed into an implantable tubular graft 5 defined by the microstructure having nodes 1, longitudinally compressed fibrils 2 and elastomeric matrix 4 within the pores 3.
Figure 6:
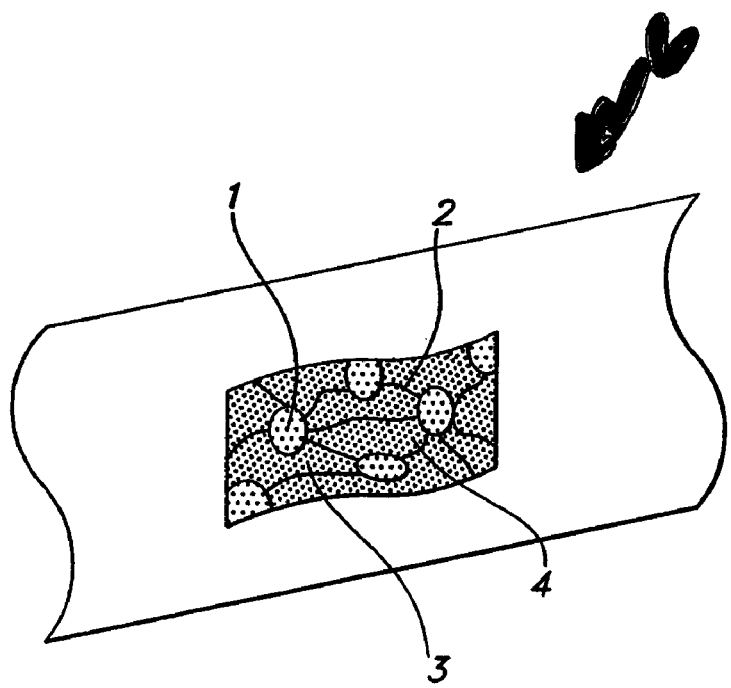
FIG. 6 is a schematic representation of the ePTFE material of the present invention formed into a patch 6 defined by the microstructure having nodes 1, longitudinally compressed fibrils 2 and elastomeric matrix 4 within the pores 3.

The above-described elastomerically recoverable ePFTE material or patch 6 was implanted in the same manner as was currently used to implant conventional ePTFE tubes, patches, grafts, or tubular stent graft, and the like as shown in FIGS. 5 and 6. Moreover, the elastomeric material minimized suture hole bleeding at the time of implantation, increased suture retention strength, reduced serious weepage, and inhibited tissue ingrowth because of its recovery and compression properties. While this invention was described with reference to preferred embodiments thereof, the description was for illustrative purposes only and was not to be construed as limiting the scope of the invention. Various modifications and changes may be made by those skilled in the art without departing from the true spirit and scope of the invention as defined by the appended claims.

EXAMPLES

Example 1

Placed 6 mm diameter ePTFE excel soft tube with 1500% expansion over a mandrel of equal diameter. Manually longitudinally compressed the tube about 50% and secured the ends of the tube with Teflon tape. While in the compressed state, applied 7.5% Corethane 2.5W30 in DMAc by brushing technique. Placed tube into oven at 110° F. to dry for 10 min. Remove from oven. Repeated the application of elastomeric material by the brushing technique 2 more times. Then, removed tube and dried after each application from mandrel. The elastomerically recoverable PTFE tube was longitudinally stretch up to 90% its original length. Once the stretching force was removed the tube recovered to its original length without deformation. The stretching and recovery was repeated multiple times without deforming the elastomerically recoverable PTFE tube.

Example 2

Placed 6 mm diameter ePTFE tube of 800% expansion, expansion velocity of 35 cm/sec, over a mandrel with similar diameter. Evenly applied the 7.5% Corethane 2.5W30 in DMAc by the spraying technique. Placed tube into oven at 110° C. for 10 min. and slightly dried the Corethane. Then, removed tube from oven, and repeated elastomeric application by the spray technique and again dried the $2^{nd}$ application. Then, removed from oven and longitudinally compressed ePTFE penetrated with elastomeric material about 50% while on the mandrel, and secured with Teflon tape. A third application of Corethane was applied by the spray technique while the tube was in the compressed state. The tube was placed in oven for 10 min. The tube was removed from the oven, and then removed from the mandrel. The tube longitudinally stretched about 300%. Upon release of stretching force the elastomerically recoverable PTFE tube recovered to original size. The stretching and recovery was repeated multiple times without deforming the material.

What is claimed is:

1. An elastomerically recoverable PTFE material, consisting essentially of:
    (a) an ePTFE material defined by nodes and fibrils, said fibrils being in a longitudinally compressed state and defining pores of a size sufficient to permit penetration of an elastomeric material wherein said eslatomeric material impregnates said pores throughout the ePTFE material without creating an exterior coating on said ePTFE material, wherein said ePTFE material is a tube, having an internal diameter, an external diameter, and a longitudinal axis, the ePTFE material having been expanded in the longitudinal direction; and
    (b) an elastomeric material having a solids content of about 7.5% to about 15% by weight within said pores; said compressed fibrils and elastomeric material cooperatively permitting longitudinal expansion between about 90% and about 300% of said longitudinally compressed state and elastomeric recovery without plastic deformation of said ePTFE material, wherein said elastomeric material is a polycarbonate urethane material having a shore hardness rating between 70A and 75D, said elastomeric material being absent from an outer surface of said tube.

2. An elastomerically recoverable PTFE material, consisting essentially of:
    (a) an ePTFE material in the form of a tube having an internal diameter and an external diameter and characterized by a longitudinal axis, the ePTFE material defined by nodes and fibrils, said fibrils being compressed in a direction parallel to the longitudinal axis and defining pores of a size sufficient to permit penetration of an elastomeric material wherein said elastomeric material impregnates said pores throughout the ePTFE material without creating an exterior coating on said ePFTE material; and p1 (b) an elastomeric material having a solids content of about 7.5% to about 15% by weight within said pores; said compressed fibrils and elastomeric material cooperatively permitting longitudinal expansion between about 90% and about 300% of said longitudinally compressed state and elastomeric recovery without plastic deformation of said ePFTE material, wherein said elastomeric material is a polycarbonate urethane material having a shore hardness rating between 70A and 75 D, said elastomeric material being absent from an outer surface of said tube material.

3. A method of producing an elastomerically recoverable PTFE structure consisting essentially of the steps of:
    (a) providing an ePTFE material defined by nodes, fibrils and pores, wherein said pores have a pore size, said pore size is a space defined by a distance between said nodes and distance between said fibrils wherein said ePTFE material is a tube, having an internal diameter and an external diameter;
    (b) subsequently compressing said fibrils of the ePTFE tube longitudinally wherein said pore size is sufficient to permit penetration of an elastomeric material within said pores;
    (c) applying an elastomeric material to said compressed fibrils in a sufficient amount to impregnate said pores of said ePTFE material wherein said elastomeric material impregnates said pores without creating an exterior coating on said ePTFE material;
    (d) partially drying said elastomeric material within said pores; and
    (e) subsequently applying at least one additional application of said elastomeric material to said pores in a sufficient amount to impregnate said pores of said ePTFE material to provide a structurally integral elasomerically recoverable ePTFE material wherein said elastomeric material impregnates said pores without creating an exterior coating on said ePTFE material; and
    (f) drying at least an additional application of said elastomeric material within said pores;
    wherein, subsequent to a final application of said elastomeric material, the elastomeric material is impregnated in said pores without the presence of an exterior coating on said ePTFE material.

4. The method according to claim 3 further comprising the step of permitting the elastomeric material to dry within said pores while said fibrils are still longitudinally compressed defining an elastomeric matrix.

5. The method according to claim 3 wherein said compressing step includes the steps of:
    (a) pulling said ePTFE tube over a mandrel having an external diameter of approximately the same dimensions as said internal diameter of the ePTFE tube; and
    (b) compressing at least a portion of the ePTFE tube along a longitudinal axis of the tube while the tube is supported by the mandrel.

6. The method according to claim 3 wherein said applying step includes the step of dip coating at least a portion of the ePTFE material with the elastomeric material.

7. The method according to claim 1 wherein said applying step includes the step of spray coating at least a portion of the ePTFE material with the elastomeric material.

8. The method according to claim 3 wherein said applying step includes the step of brushing the elastomeric material onto at least a portion of the ePTFE material.

9. The method according to claim 3 wherein said applying step comprises the step of applying elastomeric material over the entire ePTFE material, and wherein the compressing step comprises the step of compressing the ePTFE material uniformly along its entire length.

10. The method according to claim 3 wherein said elastomeric material is polyurethane.

* * * * *